United States Patent [19]

Bollens et al.

[11] Patent Number: 5,705,165
[45] Date of Patent: Jan. 6, 1998

[54] COSMETIC COMPOSITIONS CONTAINING HYDROFLUOROCARBON COMPOUNDS

[75] Inventors: Eric Bollens, Saint-Maurice; Claude Mahieu, Paris, both of France

[73] Assignee: L'Oreal, Paris, France

[21] Appl. No.: 379,530

[22] PCT Filed: Jun. 1, 1994

[86] PCT No.: PCT/FR94/00633

§ 371 Date: Mar. 21, 1995

§ 102(e) Date: Mar. 21, 1995

[87] PCT Pub. No.: WO94/27568

PCT Pub. Date: Dec. 8, 1994

[30] Foreign Application Priority Data

Jun. 2, 1993 [FR] France ..................... 93 06604

[51] Int. Cl.$^6$ ..................... A61K 7/48
[52] U.S. Cl. ..................... 424/401; 424/59; 424/61; 424/63; 424/64; 424/70.1; 424/70.6; 424/70.7; 514/844; 514/846; 514/937; 568/27; 568/32; 568/74
[58] Field of Search ..................... 568/27, 28, 32, 568/35, 74; 424/401, 59, 61, 63, 64, 70.1, 70.6, 70.9; 514/844, 846, 937

[56] References Cited

FOREIGN PATENT DOCUMENTS 2 416 222  8/1979  France.
93/11103   6/1993  WIPO.

*Primary Examiner*—Jyothsan Vennat
*Attorney, Agent, or Firm*—Jacobson, Price, Holman & Stern, PLLC

[57] ABSTRACT

The present invention concerns the use in a cosmetic composition of a hydrofluorocarbon compound with formula (I):

$$R_F-(CH_2)_n-X-[C_3H_5(OH)]-Y-R_H \qquad (I)$$

where
$C_3H_5(OH)$ represents the structures:

$$-CH_2-\underset{\underset{OH}{|}}{CH}-CH_2- \quad \text{or} \qquad (Ia)$$

$$-\underset{\underset{CH_2OH}{|}}{CH}-CH_2- \quad \text{or} \qquad (Ib)$$

$$-CH_2-\underset{\underset{CH_2OH}{|}}{CH}- \qquad (Ic)$$

$R_F$ represents a perfluorinated $C_4$–$C_{20}$ alkyl radical or a mixture of perfluorinated $C_4$–$C_{20}$ alkyl radicals;

$R_H$ represents a linear or branched $C_1$–$C_{22}$ alkyl radical or a mixture of linear or branched $C_1$–$C_{22}$ alkyl radicals, an aryl radical or an aralkyl radical;

n is between 0 and 4;

X and Y represent

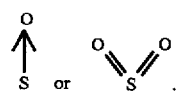

It also concerns certain sulfoxide and sulfone compounds and cosmetic compositions including the compounds of the invention.

9 Claims, No Drawings

COSMETIC COMPOSITIONS CONTAINING HYDROFLUOROCARBON COMPOUNDS

This application is a 371 of PCT/FR94 00633 filed on Jun. 1, 1994.

The present invention concerns the use of hydro- and fluorocarbon compounds in cosmetic compositions, cosmetic compositions containing these compounds and certain hydro- and fluorocarbon sulfoxides or sulfones.

Perfluoropolyethers are known for their use in cleaning, protecting or making up the skin or washing hair. These compounds are known to have a low surface tension and are easy to spread, but have very low solubility in most fluids apart from fluorine-containing fluids. This means that they are difficult to incorporate in cosmetic composition formulations. Some of these compounds, perfluoromethylisopropylethers, are sold by MONTEFLUO under the trade name "FOMBLIN HC".

We have now discovered compounds which, contrary to FOMBLIN compounds, have good solubility properties, in particular in the conventional solvents used in cosmetics, such as low alcohols, fatty substances and the usual oils. Their amphiphilic character, properties and compatibility with the solvents mean that homogeneous, stable compositions can be prepared and, for example, can ensure that the emulsions they form have good stability.

The present invention thus concerns the use of compounds with formula:

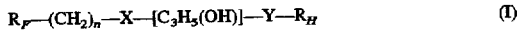

where
$C_3H_5(OH)$ represents the structures:

$R_F$ represents a perfluorinated $C_4$–$C_{20}$ alkyl radical or a mixture of perfluorinated $C_4$–$C_{20}$ alkyl radicals;

$R_H$ represents a linear or branched $C_1$–$C_{22}$ alkyl radical or a mixture of linear or branched $C_1$–$C_{22}$ alkyl radicals, an aryl radical or an aralkyl radical;

n is between 0 and 4;

X and Y represent S,

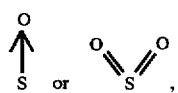

in a cosmetic composition.

Preferred compounds are those for which $R_F$ represents a perfluorinated $C_6$–$C_{12}$ alkyl radical, $R_H$ represents a linear or branched $C_3$–$C_{18}$ alkyl radical, a $C_6$–$C_{10}$ aryl radical or a $C_7$–$C_{15}$ aralkyl radical, and n equals 2.

Preferably, X and Y represent S.

Examples of linear or branched alkyl radicals are butyl, octyl, 2-ethylhexyl, decyl, dodecyl, 2-butyloctyl, hexadecyl, 2-hexyldecyl, and octadecyl radicals.

Examples of aralkyl radicals are 4-nonylphenyl and benzyl radicals, and an example of an aryl radical is the phenyl radical.

Compounds with formula (I) in accordance with the invention can be prepared by reacting a fluorine compound containing an acidic hydrogen with formula (II):

with an epoxide with formula (III):

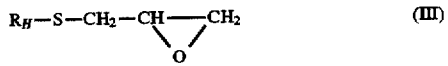

or by reacting a hydrocarbon containing an acidic hydrogen with formula (IV):

with a fluorine-containing epoxide with formula (V):

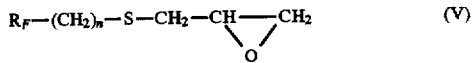

in the presence of an acidic or basic compound which acts as a reactant or as a catalyst, to produce the corresponding compound with formula (I). Substituents $R_F$, $R_H$ and n have the same meanings in formulae (II), (III), (IV) and (V) as those given for formula (I). The mercaptan function can be optionally oxidized to the sulfoxide or sulfone using an oxidizing agent, preferably hydrogen peroxide in an acidic medium.

Compounds with formula (V) are described in U.S. Pat. 3,976,698, in European patent application EP-A-0 300 358 and in German patent application DE-A-2 018 461.

The compounds which act as a reactant or as a catalyst may thus be basic, such as alkali metals, alkali or alkaline earth metal hydroxides, alkali metal alcoholates such as methylates or tertiobutylates, alkaline hydrides such as sodium hydride, or tertiary amines such as pyridine or triethylamine. They may also be Lewis bases, for example cesium, rubidium or potassium fluorides. These compounds may be supported on a solid support such as alumina. Preferably, an alkali alcoholate such as sodium methylate or a tertiary amine such as pyridine is used.

These compounds may also be acids, in particular when the starting material with formula (II) or (IV) is an alcohol. These acids may be inorganic acids or their tertiary amine salts, or Lewis acids such as boron trifluoride, tin tetrachloride, or antimony pentachloride, used neat, in solution or associated with any normal support.

A basic compound is preferably used.

The concentration of acid or basic compounds acting as reactant or catalyst and used in preparing compounds with formula (I) can be between 1% and 100% molar, preferably between 2% and 10% molar with respect to the fluorine-containing compound with an acidic hydrogen with formula (II) or (IV).

The preparation can be carried out in the presence or absence of a solvent.

Examples of solvents are aliphatic hydrocarbons such as heptane or hexane, cyclic hydrocarbons such as cyclohexane, aromatic hydrocarbons such as toluene, ethers such as ethyl ether or isopropyl ether, cyclic ethers such as dioxane, or acetonitrile, dimethylformamide, N-methylpyrrolidone, dimethylacetamide or alcohols such as methanol, ethanol or isopropanol.

The compound of the invention can be prepared by firstly mixing the compound with an acidic hydrogen with formula (II) or (IV) with the acidic or basic reactant or catalyst, in an inert atmosphere. Mixing can be carried out at a temperature of between 20° C. and 180° C., preferably between 50° C.

and 150° C. The term "inert atmosphere" means an atmosphere of nitrogen, argon or helium, for example.

Mixing can be effected in the presence or absence of a solvent, depending on the nature of the compound with an acidic hydrogen and the reactant or catalyst.

The epoxide with formula (III) or (V) is then added to the mixture obtained. Addition can be effected all at once or gradually, over a period of 30 minutes to 2 hours, for example.

The reaction time is thus between about 1 hour and 24 hours, preferably between 1 hour and 3 hours.

When it contains a mercaptan function, the compound produced by the reaction can be oxidized to a sulfoxide or sulfone in the presence of hydrogen peroxide in an acidic medium, using known methods, particularly as described in French patents FR-A-2 099 092 and FR-A-2 516 920.

It may also be necessary to neutralize the mixture obtained, and separate the synthesized compound using conventional methods, for example distillation.

When a compound with formula (I) is prepared in the presence of a basic compound, it produces only compounds in which $C_3H_5(OH)$ represents group (Ia). When the reaction is carried out in the presence of an acidic compound, a mixture of compounds can be obtained corresponding to designations (Ia), (Ib), and (Ic) of $C_3H_5(OH)$.

The compound of the invention can be in the form of an oil, or it may be solid at room temperature.

Compounds with formula (I) where X and Y represent S are known and can be used as lubricants.

A further object of the invention is to provide a compound with formula (I'):

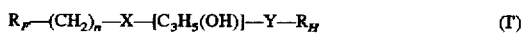

where
$C_3H_5(OH)$ represents the structures:

$R_F$ represents a perfluorinated $C_4$–$C_{20}$ alkyl radical or a mixture of perfluorinated $C_4$–$C_{20}$ alkyl radicals;

$R_H$ represents a linear or branched $C_1$–$C_{22}$ alkyl radical or a mixture of linear or branched $C_1$–$C_{22}$ alkyl radicals, an aryl radical or an aralkyl radical;

n is between 0 and 4;

X and Y represent

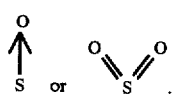

In general, these compounds are used in cosmetic compositions to improve the cosmetic properties. They provide smoothness, gloss and a non-sticky feel to keratinous material such as skin, hair and nails. In addition, some of these compounds are in the form of a colorless oil and can thus be used to produce transparent emulsions.

The invention thus also concerns a cosmetic composition containing at least one compound with formula (I) and at least one cosmetic additive.

The composition can be in the form of an emulsion, milk or cream, oily or oleoalcoholic lotion, greasy or oleoalcoholic gel, ionic or non-ionic amphiphilic lipid based vesicular dispersion, solid stick, paste, spray or aerosol foam.

Depending on the form of the composition into which the compound of the invention is incorporated, the compositions also contain additives which are normal for the selected form.

More precisely, the composition can be a skin or hair milk or cream, a make-up removing cream, lotion or milk, a sun protecting cream, gel, milk or lotion, a shaving cream or foam, an aftershave lotion, a shampoo or conditioner, a body deodorant, a toothpaste, a lacquer, a hair dye composition, a hair perming composition, a lip care product or a nail care product.

The cosmetic composition can also be used as make-up for eyelashes, eyebrows, nails, lips or for skin in epidermal treatments, a foundation, lipstick, eye-shadow, blusher, eyeliner, mascara or nail polish, for example.

Compounds with formula (I) represent 0.1% to 25%, preferably 0.1% to 15% of the total composition weight.

Examples of normal cosmetic additives which can be present in this type of composition are the usual fatty substances, organic solvents, silicones, thickeners, softeners, UV-A or UV-B or broad spectrum solar filters, anti-foaming agents, moisturising agents, humectants, fragrances, preservatives, surfactants, fillers, sequestrating agents, emulsifiers, anionic, cationic, non-ionic or amphoteric polymers and their mixtures, antiperspirants, alkalinizing agents, dyes, pigments, propellants, anti-oxidizing agents and free radical absorbers.

More precisely, examples of fatty substances are oils or waxes or their mixtures, fatty acids, fatty alcohols, fatty acid esters such as $C_6$ to $C_{18}$ fatty acid triglycerides, vaseline, paraffin, lanolin, or hydrogenated or acetylated lanolin.

Examples of oils are inorganic, animal, vegetable or synthetic oils, in particular vaseline oil, paraffin oil, castor oil, jojoba oil, sesame seed oil, and silicone and isoparaffin oils and gums.

Particular examples of animal, fossil, vegetable, inorganic or synthetic waxes are beeswax, Carouba wax, Candelilla wax, ozokerites, microcrystalline waxes and silicone waxes and resins.

Examples of organic solvents which are generally used in cosmetic compositions are $C_1$ to $C_6$ low monoalcohols or polyalcohols such as ethanol, isopropanol, propyleneglycol, glycerol, sorbitol, ketones such as acetone, esters such as butyl acetate or ethyl acetate, and toluene.

Examples of thickeners are cellulose derivatives, polyacrylic acid derivatives, guar gum or carouba gum, and xanthane gum.

Examples of surfactants are non-ionic surfactants such as alkyl($C_8$–$C_{24}$)polyglycosides where the number of glucoside units is between 1 and 15, and non-ionic polyglycerolated surfactants.

Particular alkylpolyglycosides are those sold under the trade name APG, such as APG 300, APG 350, APG 500, APG 550, APG 625 and APG base 10-12; and products sold by SEPPIC under the trade names TRITON CG 110 and TRITON CG 312.

The polyglycerolated compounds are derivatives resulting from condensation of 1 to 10, preferably 2 to 6 moles of glycidol with one mole of $C_{10}$–$C_{14}$ alcohol or alphadiol, or with $C_{12}$–$C_{18}$ fatty acid diglycolamides, such as those described in French patents FR-A-1 477 048, FR-A-2 328 763, FR-A-2 091 516 and FR-A-2 169 787.

The vesicular dispersions of ionic or non-ionic amphiphilic lipids mentioned above can be prepared using normal techniques, for example as described in "Les liposomes en biologie cellulaire et pharmacologie", Ed. INSERM/John Libbery Eurotext (1987), pp 6–18.

For toothpaste compositions, the usual additives can be used such as polishing agents, for example silica, active ingredients such as fluorides, for example sodium fluoride, and optional sweetening agents, for example sodium saccharinate.

The following examples illustrate the invention and do not in any way limit its scope.

PREPARATION EXAMPLES

EXAMPLE I 1-(2'-F-hexylethylthio)-3-octylthio-2-propanol 0.61 g of a methanolic solution of sodium methylate (about 30%—5.65 meq g$^{-1}$) was added to 10.05 g (0.069 mole) of octanethiol at a temperature of 25° C. in a stream of nitrogen.

The mixture was heated to 70° C. The methanol present in the mixture was evaporated off under vacuum.

The 2-F-hexylethylthioglycidylether (30 g—0.069 mole) was added dropwise over 30 minutes. The temperature of the mixture was maintained at 60° C. to 70° C. during addition of the epoxide.

After addition, the temperature was reduced to 25° C.

The mixture was neutralized using 3.5 ml of normal HCl.

1-(2'-F-hexylethylthio)-3-octylthio-2-propanol was separated by distillation: B Pt=178° C./66.5 Pa.

30 g (75%) of a colorless transparent oil was obtained. Elemental analysis:

|  | % C | % H | % S | % F |
| --- | --- | --- | --- | --- |
| Calculated | 39.18 | 4.67 | 11.01 | 42.40 |
| Measured | 39.16 | 4.65 | 10.57 | 42.46 |

EXAMPLE II 1-(2'-F-hexylethylsulfoxy)-3-octylsulfoxy-2-propanol

A mixture of hydrogen peroxide (110 vol)/pure acetic acid (8.5 ml/0.1 ml) was added to 11.64 g of 1-(2'-F-hexylethylthio)-3-octylthio-2-propanol (0.02 mole) over a period of 20 minutes at 5° C., with stirring. The reaction was very exothermic and the mixture solidified.

The product was transferred into 100 ml of water and then filtered through n° 4 sintered glass after vigorous stirring.

The solid residue was washed with water to a pH of 7.

12 g (98%) of a white powder was obtained which had a melting point of 145° C. The substance was 1-(2'-F-hexylethylsulfoxy)-3-octylsulfoxy-2-propanol.

Elemental analysis:

|  | % C | % H | % S | % F |
| --- | --- | --- | --- | --- |
| Calculated | 37.14 | 4.43 | 10.44 | 40.19 |
| Measured | 36.77 | 4.39 | 10.43 | 40.00 |

EXAMPLE III 1-(2'-F-hexylethylsulfonyl)-3-octylsulfonyl-2-propanol 8.7 g (0.015 mole) of 1-(2'-F-hexylethylthio-2-propanol in solution in 15 ml of acetic acid was added to a mixture of hydrogen peroxide (110 vol)/pure acetic acid/pure sulfuric acid, in the following respective proportions: 10 ml/25 ml/20 drops, at 5° C., with stirring.

Following addition, the ice bath was removed and the mixture was heated for 3 hours at 80° C.

When the temperature reached 25° C., the product, which had solidified, was transferred into 50 ml of ice water. After vigorous stirring, the white solid obtained was filtered through no 4 sintered glass, then washed to a pH of 7.

The residue obtained was dried in a vacuum oven at 40° C.

9.3 g (96%) of a white powder was obtained. The substance was 1-(2'-F-hexylethylsulfonyl)-3-octylsulfonyl-2-propanol.

Elemental analysis:

|  | % C | % H | % S | % F |
| --- | --- | --- | --- | --- |
| Calculated | 35.30 | 4.21 | 9.92 | 38.20 |
| Measured | 35.29 | 4.21 | 9.62 | 37.79 |

EXAMPLE IV 1-(2'-F-octylethylthio)-3-octadecylthio-2-propanol 2.1 g of potassium tertiobutylate was added to 107 g (0.37 mole) of octadecanethiol at a temperature of 30° C. in a stream of nitrogen, followed by 50 ml of ethanol.

The temperature of the mixture was raised to 70° C., then molten glycidyl 2-F-octylethylthioether was added over 2 hours 30 minutes (200 g—0.37 mole). The temperature was maintained at between 60° C. and 70° C. for 4 hours following addition of the epoxide.

After cooling to 25° C., the residue was taken up in 1.5 l of isopropanol at 40° C. When a clear solution had been produced, 0.1 ml of concentrated HCl was added and the precipitate was filtered. After cooling to 25° C., the mixture solidified. The mixture was centrifuged to eliminate the impurities dissolved in the isopropanol in the supernatant liquid.

The residue was dried in a vacuum oven at 40° C.

235 g of 1-(2'-F-octylethylthio)-3-octadecylthio-2-propanol was obtained in the form of a white powder.

Yield: 75%.

Melting point: 74° C.

Elemental analysis:

|  | % C | % H | % S | % F |
| --- | --- | --- | --- | --- |
| Calculated | 45.25 | 5.76 | 7.79 | 39.25 |
| Measured | 45.43 | 5.89 | 7.47 | 39.50 |

FORMULATION EXAMPLES

EXAMPLE 1

Oil-in water solar protection emulsion

| | |
| --- | --- |
| Mixture of cetylstearyl alcohol and cetylstearyl alcohol oxyethylenated with 33 moles of ethylene oxide (80/20), sold by TENSIA under the trade name | 7 g AM |

-continued

| | |
|---|---|
| DEHSCONET 390 | |
| Glyceryl stearate sold by GATTEFOSSE under the trade name GELEOL COPEAUX | 2 g |
| Silicone oil sold by RHONE POULENC under the trade name SILBIONE HUILE 70 047 V300 | 1.5 g |
| Cetyl alcohol | 1.5 g |
| Vaseline oil | 15 g |
| Compound of Example I | 0.1 g |
| Glycerol | 20 g |
| Preservatives qs | |
| Benzene 1,4-di(3-methylidene-10-camphosulfonic) acid | 4 g |
| Sterilized demineralized water qsp | 100 g |

The emulsion was produced by adding oily phase A at about 80° C. to aqueous phase B at the same temperature, with rapid stirring. An oil-in water emulsion was obtained in the form of a cream.

EXAMPLE 2

Skin cream—Oil-in-water emulsion

A skin cream was prepared in the form of an oil-in-water emulsion, with the following composition:

| | |
|---|---|
| Phase A | |
| Non-ionic hydroxypropylether surfactant obtained by condensation, with alkaline catalysis, of 3.5 moles of glycidol with a mixture of $C_{11}$-$C_{14}$ alphadiols, in accordance with French patent FR-A-2 091 516 | 2.4 g |
| Methyl parahydroxybenzoate | 0.2 g |
| Glycerine | 5 g |
| Water | 22.06 g |
| Phase A' | |
| Gel of glyceryl polyacrylate in water (50/50), sold by HISPANO CHEMICA under the trade name HISPAGEL 100 | 56.14 g |
| Phase B | |
| Cetyl alcohol | 1 g |
| Compound of Example II | 5 g |
| Apricot kernel oil | 5 g |
| Sesame seed oil | 1.5 g |
| Caprylic/capric acid triglyceride, sold by HULS under the trade name MIGLYOL 812 | 1.5 g |
| Propyl parahydroxybenzoate | 0.2 g |

Method

Phase A was heated to 80° C. Phase A' was added, with stirring, followed by phase B which had been heated to 80° C. The mixture was allowed to cool to room temperature, maintaining the stirring.

EXAMPLE 3

Skin cream—Oil-in-water emulsion

A skin cream was prepared in the form of an oil-in-water emulsion, with the following composition:

| | |
|---|---|
| Phase A | |
| Non-ionic hydroxypropylether surfactant obtained by condensation, with alkaline catalysis, of 3.5 moles of glycidol with a mixture of $C_{11}$-$C_{14}$ alphadiols, in accordance with French patent FR-A-2 091 516 | 2.4 g |
| Methyl parahydroxybenzoate | 0.2 g |
| Glycerine | 5 g |
| Water | 22.06 g |
| Phase A' | |
| Gel of glyceryl polyacrylate in water (50/50), sold by HISPANO CHEMICA under the trade name HISPAGEL 100 | 56.14 g |
| Phase B | |
| Cetyl alcohol | 1 g |
| Compound of Example III | 5 g |
| Apricot kernel oil | 5 g |
| Sesame seed oil | 1.5 g |
| Caprylic/capric acid triglyceride, sold by HULS under the trade name MIGLYOL 812 | 1.5 g |
| Propyl parahydroxybenzoate | 0.2 g |

Method

Phase A was heated to 80° C. Phase A' was added, with stirring, followed by phase B which had been heated to 80° C. The mixture was allowed to cool to room temperature, maintaining the stirring.

EXAMPLE 4

Skin cream—Oil-in-water emulsion

A skin cream was prepared in the form of an oil-in-water emulsion, with the following composition:

| | |
|---|---|
| Phase A | |
| Non-ionic hydroxypropylether surfactant obtained by condensation, with alkaline catalysis, of 3.5 moles of glycidol with a mixture of $C_{11}$-$C_{14}$ alphadiols, in accordance with French patent FR-A-2 091 516 | 2.4 g |
| Methyl parahydroxybenzoate | 0.2 g |
| Glycerine | 5 g |
| Water | 22.06 g |
| Phase A' | |
| Gel of glyceryl polyacrylate in water (50/50), sold by HISPANO CHEMICA under the trade name HISPAGEL 100 | 56.14 g |
| Phase B | |
| Cetyl alcohol | 1 g |
| Compound of Example IV | 5 g |
| Apricot kernel oil | 5 g |
| Sesame seed oil | 1.5 g |
| Caprylic/capric acid triglyceride, sold by HULS under the trade name MIGLYOL 812 | 1.5 g |
| Propyl parahydroxybenzoate | 0.2 g |

Method

Phase A was heated to 80° C. Phase A' was added, with stirring, followed by phase B which had been heated to 80° C. The mixture was allowed to cool to room temperature, maintaining the stirring.

EXAMPLE 5

Lipstick

A lipstick was prepared with the following composition:

| | |
|---|---|
| Compound of Example I | 1 g |
| Ozokerite | 14.90 g |
| Microcrystalline wax | 4.90 g |
| Candelilla wax | 7.40 g |
| Jojoba oil | 6.20 g |
| Castor oil | 1.20 g |
| Liquid lanoline | 18.60 g |
| Acetylated lanoline | 9.90 g |
| Vaseline oil | 11.10 g |
| Talc | 3.70 g |
| Micatitanium | 8.70 g |
| D & C Red no 7 Ca lake | 5.20 g |
| D & C Red no 7 Ba lake | 2.80 g |
| FD & C Yellow no 5 | 1 g |
| Titanium dioxide | 3.10 g |
| Butylhydroxytoluene | 0.30 g |
| Fragrance qs | |

The oils were mixed at a temperature of 50° C. to 60° C. The pigments and organic lacquers were ground in the oily phase.

The molten waxes were then added, followed by the talc and the micatitanium, then the fragrance.

The composition was then poured into a mold.

The lipstick was easy to apply (slid on easily) and made the lips soft.

The compound of Example I could be replaced by the compound of Example IV.

EXAMPLE 6

Nail polish

A nail polish was prepared with the following composition:

| | |
|---|---|
| Compound of Example I | 1 g |
| Nitrocellulose | 10.75 g |
| Toluene sulfonamide formaldehyde resin, sold by AKZO under the trade name KETJENFLEX MS80 | 9.70 g |
| Tributyl acetylnitrate sold by PFIZER under the trade name CITROFLEX A4 | 6.45 g |
| Toluene | 30.70 g |
| Butyl acetate | 21.50 g |
| Ethyl acetate | 9.20 g |
| Isopropyl alcohol | 7.70 g |
| Citric acid | 0.05 g |
| Stearalkonium hectorite | 1.45 g |
| Pigments | 1.50 g |

The polish was easy to apply to the nail to give a film which adhered well to the nail and had a high gloss. The gloss was retained for a long period.

EXAMPLE 7

Shampoo

| | |
|---|---|
| Laurylether carboxylate, sodium salt ($C_{12}/C_{14}$ 70/30) oxyethylenated with 4.5 moles of ethylene oxide in 22% aqueous solution, sold by CHEM-Y under the trade name AKYPOSOFT | 7.7 g AM |
| Laurylether sulfate, sodium salt ($C_{12}/C_{14}$ 70/30) oxyethylenated with 2.2 moles of ethylene oxide in 28% aqueous solution, sold by MARCHON under the trade name EMPICOL ESB/3 FL | 8.4 g AM |
| Hydroxyethylcellulose crosslinked with epichlorhydrine quaternized with trimethylamine, sold by NATIONAL STARCH under the trade name CELQUAT SC 240 | 0.95 g |
| Coprah acid monoisopropanolamide | 3 g |
| Tallow, oxyethylenated with 60 moles of ethylene oxide myristylglycol ether (MW 3000), sold by AZKO under the trade name ELFACOS GT 282S | 0.5 g |
| Compound of Example I | 1 g |
| Preservative, fragrance | |
| Water qsp | 100 g |

The pH was adjusted to 6 using hydrochloric acid.

EXAMPLE 8

Shampoo

| | |
|---|---|
| Alkyl($C_9/C_{10}/C_{11}$ 20/40)polyglycoside 1.4 in 50% solution, sold by HENKEL under the trade name APG 300 | 10 g AM |
| Laurylether sulfate, sodium salt ($C_{12}/C_{14}$ 70/30), oxyethylenated with 2.2 moles of ethylene oxide in 28% aqueous solution, sold by MARCHON under the trade name EMPICOL ESB/3 FL | 5 g AM |
| Coprah acid monoisopropanolamide | 3 g |
| Mixture of cetylstearyl alcohol and cetylstearyl alcohol oxyethylenated with 33 moles of ethylene oxide, sold by TENSIA under the trade name DEHSCONET 390 | 2.5 g |
| Compound of Example IV | 0.5 g |
| Preservatives, fragrances, dyes | |
| Water qsp | 100 g |

The pH was adjusted to 7 using hydrochloric acid.

EXAMPLE 9

Styling lotion

| | |
|---|---|
| Methylvinylether/butyl monomaleate copolymer, 50% in ethanol, sold by ISP under the trade name GANTREZ ES 425, neutralized to 100% with 2-amino-2-methyl-1-propanol | 1 g AM |
| Compound of Example I | 0.1 g |
| Absolute ethanol | 52 g |
| Water qsp | 100 g |

EXAMPLE 10

Direct hair dye

| | |
|---|---|
| N-(β-hydroxyethyl)-1-amino-2-nitro-N,N'-bis-(β-hydroxyethyl)-4-aminobenzene | 1 g |
| (4-nitro-3-methylamino)phenoxyethanol | 0.1 g |
| N',N'-bis(β-hydroxyethyl)-4-amino-2-nitro-N-(γ-hydroxypropyl)-1-aminobenzene | 0.7 g |
| 4-amino, 2'-methyl,4'-[N,N-bis-(β-hydroxyethyl)amino]phenylazobenzene | 0.1 g |
| 3-nitro-4-β-hydroxyethylaminophenol | 0.1 g |

| | |
|---|---|
| Oleic diethanolamine | 3 g |
| Lauric acid | 1 g |
| 2-ethoxyethanol | 5 g |
| Hydroxyethylcellulose sold by UNION CARBIDE under the trade name CELLOSIZE WPO 3H | 2 g |
| Compound of Example I | 0.5 g |
| 2-amino-2-methyl-1-propanol qs | pH = 9.5 |
| Water qsp | 100 g |

The composition was applied to 90% white permed gray hair and left for 30 minutes. The hair was then rinsed, washed, rinsed again, then dried. The hair had been tinted a dark violine chestnut.

EXAMPLE 11

A toothpaste was prepared by mixing the following ingredients:

| | |
|---|---|
| Compound of Example I | 0.5 g |
| Powdered lauryl sulfate, sodium salt, 93% AM, sold by MARCHON under the trade name EMPICOL LZV/E | 1.5 g AM |
| Hydrated alumina sold by SOCHALU under the trade name ALUMINE SH 100 | 48 g |
| Xanthane gum sold by RHONE POULENC under the trade name RHODICARE S | 1.2 g |
| Titanium oxide | 1 g |
| Sorbitol, 70% AM in aqueous solution | 7 g AM |
| Glycerine | 8 g |
| Sodium fluoride | 0.22 g |
| Methyl parahydroxybenzoate | 0.2 g |
| Sodium saccharinate | 0.15 g |
| Flavoring qs | |
| Water qsp | 100 g |

EXAMPLE 12

Antiperspirant stick

| | |
|---|---|
| Compound of Example IV | 1 g |
| Stearyl alcohol | 20 g |
| Isopropyl myristate | 10 g |
| Talc | 1 g |
| Pyrogenized silica sold by DEGUSSA under the trade name AEROSIL R 972 | 0.5 g |
| Aluminum chloride sold by REHEIS under the trade name REACH 501 | 15 g |
| Fragrance qs | |
| Cyclomethicone sold by DOW CORNING under the trade name DC 245 FLUID qsp | 100 g |

EXAMPLE 13

Perm lotion

A reducing permanent wave lotion for hair was prepared by mixing the following ingredients:

| | |
|---|---|
| Thioglycolic acid | 9 g |
| Oleic acid oxyethylenated with 20 moles of ethylene oxide, sold by ICI under the trade name BRIJ 98 | 2 g |
| Compound of Example I | 0.2 g |
| Ammonia qs | pH = 8.2 |
| Demineralized water qsp | 100 g |

This composition was applied to wet hair which had been set onto rollers. After leaving the composition to act for a period of 15 minutes the hair was thoroughly rinsed and then the following oxidizing composition was applied:

| | |
|---|---|
| Hydrogen peroxide qs | 8 volumes |
| Oleic acid oxyethylenated with 20 moles of ethylene oxide, sold by ICI under the trade name BRIJ 98 | 0.5 g |
| Compound of Example I | 0.1 g |
| Phosphoric acid qs | pH = 3.5 |
| Demineralized water qsp | 100 g |

The oxidizing composition was allowed to act for about 5 minutes and then the rollers were removed and the hair was thoroughly rinsed with water. After drying under a hood the hair had beautiful curls.

We claim:

1. A cosmetic composition consisting essentially of at least one compound having formula (I):

$$R_F-(CH_2)_n-X-[C_3H_5(OH)]-Y-R_H \quad (I)$$

where
$C_3H_5(OH)$ represents one of the structures:

$$-CH_2-CH-CH_2- \quad \text{or} \quad \text{(Ia)}$$
$$\phantom{-CH_2-}|\phantom{CH-CH_2-}$$
$$\phantom{-CH_2-}OH$$

$$-CH-CH_2- \quad \text{or} \quad \text{(Ib)}$$
$$|$$
$$CH_2OH$$

$$-CH_2-CH- \quad \text{(Ic)}$$
$$\phantom{-CH_2-}|$$
$$\phantom{-CH_2-}CH_2OH$$

$R_F$ represents a perfluorinated $C_4-C_{20}$ alkyl radical or a mixture of perfluorinated $C_4-C_{20}$ alkyl radicals;

$R_H$ represents a linear or branched $C_1-C_{22}$ alkyl radical or a mixture of linear or branched $C_1-C_{22}$ alkyl radicals, an $C_6-C_{10}$ aryl radical or an $C_7-C_{15}$ aralkyl radical;

n is between 0 and 4;

X and Y represent S,

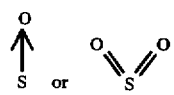

and at least one cosmetic additive.

2. A cosmetic composition according to claim 1 where in the additive is selected from the group consisting of fatty substances, organic solvents, silicones, thickeners, softeners, UV-A, UV-B and broad spectrum solar filters, anti-foaming agents, moisturising agents, humectants, fragrances, preservatives, surfactants, fillers, sequestrating agents, emulsifiers, anionic, cationic, non-ionic and amphoteric polymers and their mixtures, antiperspirants, alkalinizing agents, dyes, pigments, propellants, anti-oxidizing agents and free radical absorbers.

3. A cosmetic composition according to claim 1 wherein, in formula (I), $R_F$ represents a perfluorinated $C_6-C_{12}$ alkyl radical, $R_H$ represents a linear or branched $C_3-C_{18}$ alkyl radical, a $C_6-C_{10}$ aryl radical or a $C_7-C_{15}$ aralkyl radical, n equals 2, and X and Y represent S.

4. A cosmetic composition according to claim 1 which is in the form of a milk, cream, oily or oleoalcoholic lotion, oily or oleoalcoholic gel, ionic or non-ionic amphiphilic lipid based vesicular dispersion, solid stick, paste, spray or aerosol foam.

5. A cosmetic composition according to claim 1 which is selected from the group consisting of a skin or hair product, a make-up removing product, a sun protecting product, a shaving cream or foam, an aftershave lotion, a shampoo or conditioner, a body deodorant, a toothpaste, a lacquer, a hair dye composition, a hair perming composition, a lip care product and a nail care product.

6. A cosmetic composition according to claim 1 characterized in that it comprises 0.1% to 25% by weight of the compound with formula (I).

7. A compound with formula:

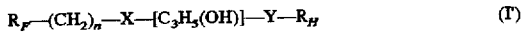 (I')

where
$C_3H_5(OH)$ represents the structures:

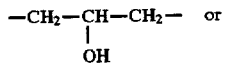 or (Ia)

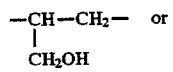 or (Ib)

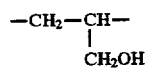 (Ic)

$R_F$ represents a perfluorinated $C_4$–$C_{20}$ alkyl radical or a mixture of perfluorinated $C_4$–$C_{20}$ alkyl radicals;

$R_H$ represents a linear or branched $C_1$–$C_{22}$ alkyl radical or a mixture of linear or branched $C_1$–$C_{22}$ alkyl radicals, a $C_6$–$C_{10}$ aryl radical or a $C_7$–$C_{15}$ aralkyl radical;

n is between 0 and 4;

X and Y represent

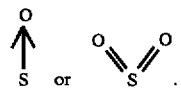

8. A compound according to claim 7 wherein:

$R_F$ represents a perfluorinated $C_6$–$C_{12}$ alkyl radical;

$R_H$ represents a linear or branched $C_3$–$C_{18}$ alkyl radical, a $C_6$–$C_{10}$ aryl radical or a $C_7$–$C_{15}$ aralkyl radical; and n equals 2.

9. A process for the cosmetic treatment of keratinous material comprising applying to the keratinous material the cosmetic composition of claim 1.

* * * * *